(12) United States Patent
Purcell et al.

(10) Patent No.: US 10,925,899 B2
(45) Date of Patent: Feb. 23, 2021

(54) COMPOSITION FOR ENERGY SUPPLEMENTATION

(71) Applicants: Marc Purcell, Québec (CA); Nathalie Miller, Quebec (CA)

(72) Inventors: Marc Purcell, Québec (CA); Nathalie Miller, Quebec (CA)

(*) Notice: Subject to any disclaimer, the term of this patent is extended or adjusted under 35 U.S.C. 154(b) by 17 days.

(21) Appl. No.: 16/067,290

(22) PCT Filed: Dec. 22, 2016

(86) PCT No.: PCT/CA2016/051524
§ 371 (c)(1),
(2) Date: Jun. 29, 2018

(87) PCT Pub. No.: WO2017/113010
PCT Pub. Date: Jul. 6, 2017

(65) Prior Publication Data
US 2019/0022140 A1    Jan. 24, 2019

Related U.S. Application Data

(60) Provisional application No. 62/272,104, filed on Dec. 29, 2015.

(51) Int. Cl.

| | | |
|---|---|---|
| *A61K 33/42* | (2006.01) | |
| *A23L 33/105* | (2016.01) | |
| *A23L 33/16* | (2016.01) | |
| *A61K 31/7076* | (2006.01) | |
| *C12P 19/32* | (2006.01) | |
| *C12N 5/04* | (2006.01) | |
| *A23L 2/38* | (2021.01) | |
| *A23L 33/13* | (2016.01) | |
| *A23L 2/52* | (2006.01) | |
| *A61K 36/21* | (2006.01) | |
| *A23L 2/56* | (2006.01) | |
| *A23L 2/58* | (2006.01) | |
| *A61K 9/00* | (2006.01) | |
| *A61K 36/18* | (2006.01) | |
| *A61K 41/00* | (2020.01) | |

(52) U.S. Cl.
CPC .............. *A61K 33/42* (2013.01); *A23L 2/38* (2013.01); *A23L 2/52* (2013.01); *A23L 2/56* (2013.01); *A23L 2/58* (2013.01); *A23L 33/105* (2016.08); *A23L 33/13* (2016.08); *A23L 33/16* (2016.08); *A61K 9/0095* (2013.01); *A61K 31/7076* (2013.01); *A61K 36/18* (2013.01); *A61K 36/21* (2013.01); *A61K 41/00* (2013.01); *C12N 5/04* (2013.01); *C12P 19/32* (2013.01); *A23V 2002/00* (2013.01)

(58) Field of Classification Search
CPC .... A61K 31/7076; A61K 9/0095; C12N 5/04; A23L 33/105; A61P 3/02
See application file for complete search history.

(56) References Cited

U.S. PATENT DOCUMENTS

| | | | | |
|---|---|---|---|---|
| 5,200,399 A | * | 4/1993 | Wettlaufer | ............... A01N 1/02 424/195.15 |
| 6,723,767 B2 | | 4/2004 | Rapaport | |
| 2009/0247633 A1 | * | 10/2009 | Crombie | ................ A61K 31/22 514/560 |
| 2011/0008867 A1 | | 1/2011 | Zarur | |

FOREIGN PATENT DOCUMENTS

JP        2014076041 A   *   5/2014

OTHER PUBLICATIONS

Raw Spinach (https://nutritiondata.self.com/facts/vegetables-and-vegetable-products/2626/2) available Feb. 9, 2014, pp. 1-4 Year: 2014).*
V8 Press Release (https://www.campbellsoupcompany.com/newsroom/press-releases/v8-rejuvenates-the-juice-aisle-with-four-new-vegetable-blend-beverages/) Feb. 6, 2015. pp. 1-11 (Year: 2015).*
Reddy, A. et al. "The pH of beverages available to the American consumer" J Am Dent Assoc. Apr. 2016; 147(4): 255-263 (Year: 2016).*
V8 Healthy Greens (https://www.campbells.com/v8/v8-fruit-and-vegetable-blends/healthy-greens/) 2019, pp. 1-3 (Year: 2019).*
Viscosity Scales (http://files.smooth-on.com/viscosity_chart.pdf) 2019, p. 1 (Year: 2019).*
Drews, H.J. "Analysis of Free Sugars and Chlorophyll in Spinach From a Local Retail Market" Master's Thesis, University of Tennessee, 1996, pp. 1-90 (Year: 1996).*
Mountain Rose Herbs (https://blog.mountainroseherbs.com/ode-spinach-powder) 2012, pp. 1-3 (Year: 2012).*
North Bay Trading (http://www.northbaytrading.com/freeze-dried-spinach) available Oct. 18, 2014, pp. 1-2 (Year: 2014).*
Soups Online (http://www.soupsonline.com/p-880-desert-gardens-chipotle-spinach-dip-mix.aspx) available Jan. 2, 2014, pp. 1-3 (Year: 2014).*
Google translation of JP-2014076041-A, published May 1, 2014, pp. 1-21 (Year: 2014).*
Graan and Ort, "Factors Affecting the Development of the Capacity for ATP Formation in Isolated Chloroplasts", Biochimica et Biophysica Acta, 637 (1981) 447-456.
Jager et al., "Oral adenosine-5'-triphosphate (ATP) administration increases blood flow following exercise in animals and humans", Journal of the International Society of Sports Nutrition 2014, 11:28.
Wilson et al., Effects of oral adenosine-5'-triphosphate supplementation on athletic performance, skeletal muscle hypertrophy and recovery in resistance-trained menw, Nutrition & Metabolism 2013, 10:57.

(Continued)

*Primary Examiner* — Andrew S Rosenthal
(74) *Attorney, Agent, or Firm* — Christian Cawthorn; Norton Rose Fulbright Canada LLP

(57) ABSTRACT

The present invention relates to a composition for the synthesis of ATP as an energy supplementation. The composition comprises a plant extract or a plant fraction suitable to produce ATP upon exposure to light. The present invention also relates to the isolation of such plant extract and to its use in energy drinks.

7 Claims, 8 Drawing Sheets

(56) References Cited

OTHER PUBLICATIONS

International Search Report of PCT/CA2016/051524.
Biology Wiki : "Main Page/BIOL 4160/Light-Induced ATP Production in Isolated Chloroplasts—Biology Wiki'", Aug. 23, 2013 (Aug. 23, 2013), XP55599739, Retrieved from the Internet: URL: http ://biologywiki.apps01.yorku.ca/index.php?title=Main_Page/BIOL-4160/Light-Induced_ATP_Production_in_Isolated_Chloroplasts [retrieved on Jun. 26, 2019] * the whole document *.
Haim Hardt et al, Plant Physiology, vol . 62, No. 1, Jul. 1, 1978 (Jul. 1, 1978), pp. 59-63.
Database BIOSIS [Online] Biosciences Information Service, Philadelphia, PA, US; 1976, Ort D R et al: "Photo Phosphorylation As a Function of Illumination Time Part 1 Effect of Permeant Cations and Permeant Anions", XP002792425. Database accession No. PREV 197763029326 * abstract *.
Database BIOSIS [Online] Biosciences Information Service, Philadelphia, PA, US; 1976, Shmeleva V L et al: , "Functional Capacity of Chloroplasts in Pea Plants Grown At Various Illuminations", XP002792427, Database accession No. PREV197764023102 * abstract *.
Database BIOSIS [Online] Biosciences Information Service, Philadelphia, PA, US; 1978, Cohen W S: "The Coupling of Electron Flow to ATP Synthesis in Pea Chloroplasts Stored in the Presence of Glycerol At Minus 70 Celsius", XP002792426, Database accession No. PREV197866054617 * abstract *.
Database BIOSIS [Online] Biosciences Information Service, Philadelphia, PA, US; 1981, Graan T et al:, "Factors Affecting the Development of the Capacity for ATP Formation in Isolated Chloroplasts", XP002792428, Database accession No. REV198273042249 * abstract *.
A V Trebst et al, The Journal of Biological Chemistry, Nov. 1, 1959 (Nov. 1, 1959), pp. 3055-3058.
Hernandez-Gil R et al, 1973, Plant Physiology (Rockville), vol. 51, NR. 2, pp. 245-249.
Database GNPD [Online] MINTEL; Apr. 30, 2013 (Apr. 30, 2013),anonymous: "Freeze Dried Spinach Powder" XP55696229, retrieved from www.gnpd.com Database accession No. 2058025.
Hincha, D. K., Höfner, R. Schwab, K. B., Heber, U., & Schmitt, J. M. (1987); Membrane rupture is the common cause of damage to chloroplast membranes in leaves injured by freezing or excessive wilting. Plant physiology, 83(2), 251-253.
Heber, U. W., & Santarius, K. A. (1964); Loss of adenosine triphosphate synthesis caused by freezing and its relationship to frost hardiness problems. Plant physiology, 39(5), 712.

* cited by examiner

COMPOSITION FOR ENERGY SUPPLEMENTATION

TECHNICAL FIELD OF THE INVENTION

The present invention relates to an energy drink and a composition to be used in an aqueous drink, capable of generating ATP as a source of energy. The present invention also relates to a method for obtaining such drink and composition, and the use of same.

BACKGROUND OF THE INVENTION

Adenosine-5'-triphosphate (ATP) transports chemical energy within cells for metabolism. It is one of the end products of photophosphorylation, cellular respiration, and fermentation and used by enzymes and structural proteins in many cellular processes, including biosynthetic reactions, motility, and cell division (Campbell, Neil A.; Brad Williamson; Robin J. Heyden (2006). *Biology Exploring Life*. Boston, Mass.: Pearson Prentice Hall.) One molecule of ATP contains three phosphate groups, and it is produced by a wide variety of enzymes, including ATP synthase, from adenosine diphosphate (ADP) or adenosine monophosphate (AMP) and various phosphate group donors. Substrate-level phosphorylation, oxidative phosphorylation in cellular respiration, and photophosphorylation in photosynthesis are three major mechanisms of ATP biosynthesis.

The structure of this molecule consists of a purine base (adenine) attached to the 1' carbon atom of a pentose sugar (ribose). Three phosphate groups are attached at the 5' carbon atom of the pentose sugar. ATP is also incorporated into nucleic acids by polymerases in the processes of DNA replication and transcription. When ATP is used in DNA synthesis, the ribose sugar is first converted to deoxyribose by ribonucleotide reductase. ATP consists of adenosine—itself composed of an adenine ring and a ribose sugar—and three phosphate groups (triphosphate). The phosphoryl groups, starting with the group closest to the ribose, are referred to as the alpha ($\alpha$), beta ($\beta$), and gamma ($\gamma$) phosphates. ATP is highly soluble in water and is quite stable in solutions between pH 6.8-7.4, but is rapidly hydrolysed at extreme pH.

ATP is an unstable molecule in water, since it will hydrolyze into ADP and phosphate. This is because the strength of bonds between phosphate residues in ATP are less than the strength of the "hydration" bonds between its products (ADP+phosphate), and water. Thus, if ATP and ADP are in chemical equilibrium in water, almost all the ATP will be converted to ADP. Any system that is far from equilibrium contains potential energy, and is capable of doing work. Living cells maintain the ratio of ATP to ADP at a point ten orders of magnitude from equilibrium, with ATP concentrations a thousand fold higher than the concentration of ADP. This displacement from equilibrium means that the hydrolysis of ATP in the cell releases a great amount of energy ATP is commonly referred to as a "high energy molecule"; however by itself, this is incorrect. A mixture of ATP and ADP at equilibrium in water can do no useful work at all. Similarly, ATP does not contain "high-energy bonds," rather the "high-energy bonds" are between its products and water, and the bonds within ATP are notable simply for being of lower energy than the new bonds produced when ATP reacts with water. Any other unstable system of potentially reactive molecules would serve as a way of storing energy, if the cell maintained their concentration far from the equilibrium point of the reaction.

The amount of energy released from hydrolysis of ATP can be calculated from the changes in energy under non-natural conditions. The net change in heat energy (enthalpy) at standard temperature and pressure of the decomposition of ATP into hydrated ADP and hydrated inorganic phosphate is −20.5 kJ/mol, with a change in free energy of 3.4 kJ/mol. The energy released by cleaving either a phosphate (Pi) or pyrophosphate (PPi) unit from ATP, with all reactants and products at their standard states of 1 M concentration, are:

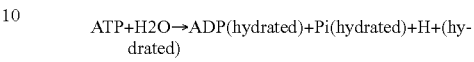

$\Delta G°=-30.54$ kJ/mol (−7.3 kcal/mol)

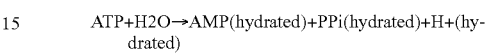

$\Delta G°=-45.6$ kJ/mol (−10.9 kcal/mol)

These values can be used to calculate the change in energy under physiological conditions and the cellular ATP/ADP ratio. The values given for the Gibbs free energy for this reaction are dependent on a number of factors, including overall ionic strength and the presence of alkaline earth metal ions such as $Mg^{2+}$ and $Ca^{2+}$. Under typical cellular conditions, $\Delta G$ is approximately −57 kJ/mol (−14 kcal/mol) (Gajewski et al. 1986).

The ATP concentration inside the cell is typically 1-10 mM. ATP can be produced by redox reactions using simple and complex sugars (carbohydrates) or lipids as an energy source. For ATP to be synthesized from complex fuels, they first need to be broken down into their basic components. Carbohydrates are hydrolysed into simple sugars, such as glucose and fructose. Fats (triglycerides) are metabolized to give fatty acids and glycerol. Most of the ATP synthesized in the mitochondria will be used for cellular processes in the cytosol; thus it must be exported from its site of synthesis in the mitochondrial matrix. The inner membrane contains an antiporter, the ADP/ATP translocase, which is an integral membrane protein used to exchange newly-synthesized ATP in the matrix for ADP in the intermembrane space (Dahout-Gonzalez et al. 2006). This translocase is driven by the membrane potential, as it results in the movement of about 4 negative charges out of the mitochondrial membrane in exchange for 3 negative charges moved inside. However, it is also necessary to transport phosphate into the mitochondrion; the phosphate carrier moves a proton in with each phosphate, partially dissipating the proton gradient.

The total quantity of ATP in the human body is about 0.1 mole. The majority of ATP is not usually synthesized de novo, but is generated from ADP by the aforementioned processes. Thus, at any given time, the total amount of ATP+ADP remains fairly constant.

The energy used by human cells requires the hydrolysis of 100 to 150 moles of ATP daily which is around 50 to 75 kg. Typically, a human will use up their body weight of ATP over the course of the day. This means that each ATP molecule is recycled 1000 to 1500 times during a single day (100/0.1=1000). ATP cannot be stored, hence its consumption closely follows its synthesis.

Functions in cells. ATP is generated in the cell by energy-consuming processes and is broken down by energy-releasing processes. In this way ATP transfers energy between spatially-separate metabolic reactions. ATP is the main energy source for the majority of cellular functions. This includes the synthesis of macromolecules, including DNA, RNA, and proteins. ATP also plays a critical role in the transport of macromolecules across cell membranes, e.g.

exocytosis and endocytosis. In the synthesis of the nucleic acid RNA, ATP is one of the four nucleotides incorporated directly into RNA molecules by RNA polymerases. The energy driving this polymerization comes from cleaving off a pyrophosphate (two phosphate groups). The process is similar in DNA biosynthesis, except that ATP is reduced to the deoxyribonucleotide dATP, before incorporation into DNA (Joyce and Steitz 1995). ATP is critically involved in maintaining cell structure by facilitating assembly and disassembly of elements of the cytoskeleton. In a related process, ATP is required for the shortening of actin and myosin filament crossbridges required for muscle contraction. This latter process is one of the main energy requirements of animals and is essential for locomotion and respiration.

The production of ATP using the energy of sunlight is called photophosphorylation. Only two sources of energy are available to living organisms: sunlight and oxidation-reduction (redox) reactions. All organisms produce ATP, which is the universal energy currency of life. In photophosphorylation, light energy is used to create a high-energy electron donor and a lower-energy electron acceptor. Electrons then move spontaneously from donor to acceptor through an electron transport chain.

In plants, ATP is synthesized in thylakoid membrane of the chloroplast during the light-dependent reactions of photosynthesis in a process called photophosphorylation. Here, light energy is used to pump protons across the chloroplast membrane. This produces a proton-motive force and this drives the ATP synthase, exactly as in oxidative phosphorylation (Allen, 2002).

One function of the inner membrane of the chloroplast, the thylakoid, is to pump $H^+$ of the media to initiate photosynthesis. This process is very important to preserve the membrane and the synthesis of ATP from very acidic media like the stomach.

The chloroplast is a fragile organite; the inner and outer osmolarity could be in equilibrium to preserve it. The liquid containing the chloroplast must have a viscosity from 2 to 10 centipoise.

Neuhaus et al. (U.S. Pat. No. 6,891,088) describes transgenic plant cells and plants exhibit an increase or a decrease of the plastidial ADP/ATP translocator activity.

Bandman et al. (U.S. Pat. No. 6,020,474) provides two ATP synthase subunits (designated individually as Asy-1 and Asy-2, and collectively as Asy) and polynucleotides which identify and encode Asy. The invention also provides genetically engineered expression vectors and host cells comprising the nucleic acid sequences encoding Asy and a method for producing Asy.

Hiyoshi et al. (U.S. Pat. No. 5,824,862) provides a DNA encoding ATP dependent fructose 6-phosphate 1-phosphotransferase originating from a plant, as well as a recombinant vector comprising the DNA and a plant transformed with the DNA.

Elseviers et al. (U.S. Pat. No. 6,296,892) discloses an isotonic beverage product for direct increase of the muscular ATP level consisting essentially of a solution of D-ribose and blood glucose increasing monosaccharides and oligosaccharides and/or hydrogenated glucose syrups. These drinks serve to increase the overall performance during physical exercise and at the same time diminish fatigue.

Hamway et al. (U.S. Pat. Nos. 9,162,804 and 9,090,387) discloses a dispensing cap for attaching to a container, which includes a dispensing chamber having an interior compartment for holding an ingredient to be dispensed into the container.

Study measuring the ATP level in red blood show that person in seventies have 50% less ATP than young person in the twenty. This decrease could be responsible for the high blood pressure due to ageing. Patients with primary pulmonary hypertension suffer from ATP liberation failure by red blood cells (Sprague et al., 2001). It is also true with patients suffer from mucoviscidose who develop also a pulmonary hypertension (Sprague et al., 1998).

During vigorous activity, the ATP needs is around 500 g per minute; so the ATP reserve should be for 5 to 8 seconds only. It is evident that ATP should be constantly and efficiently synthesized to bring a constant reserve of energy. If an interruption of the supply of energy substances happens, ATP production is affected, and a cascade of radical damage begins.

Several studies show significant advantages with ATP supplementation. The first studies on exogenous administration of ATP are performed on injectable solutions intravenously; and was absorbed efficiently. Other studies administrated ATP orally. One of them, on rabbit, show after 14 days, a decrease in peripheral vascular resistance, pulmonary resistance, respiratory frequency, without any incidence on blood pressure nor cardiac rhythm (Agteresch et al., 2000). The same research group observed that the oral administration of ATP to rats during 30 days, increase the intestine capability to capture purine from intraluminal nucleosides and export ATP in blood stream. Wilson et al. (2013) clearly describe the positive effect of oral ATP supplementation on athletic performance, especially enhance muscular adaptations. Oral ATP administration can increase post-exercise blood flow, and may be particularly effective during exercise recovery (Jager et al. 2014).

Rapaport et al. (U.S. Pat. Nos. 4,880,918; 5,049,372; 5,227,371; 5,547,942; 6,723,737) teach a source of ATP administrable orally.

SUMMARY OF THE INVENTION

One aspect of the present invention provides a composition for energy supplementation, the composition comprising isolated chloroplasts and phosphorus. The composition is preferably dehydrated and upon rehydration, the composition produces ATP upon exposure to light.

In a further aspect, the chloroplasts comprises minimally functional thylakoid and chloroplastic membranes able to produce ATP in the presence of light, but may comprises further elements useful for the photosynthesis process.

In a still further aspect, there is provided a composition for the synthesis of ATP as an energy supplementation, the composition comprising a plant extract or a plant fraction suitable to produce ATP upon exposure to light, water, and phosphorus, particularly, immediately prior to ingestion/consumption.

A further aspect of the invention is provided in a composition comprising a plant extract or a plant fraction comprising chloroplasts in admixture with a carrier material.

Another aspect of the invention is provided in a composition comprising a plant extract or a plant fraction consisting of chloroplasts in admixture with a carrier material. The composition is suitable for the synthesis of ATP upon exposure to light and water.

Particularly, the plant extract used in the invention comprises chloroplasts comprising functional thylakoid and chloroplastic membranes able to produce ATP in the presence of light and water.

Chloroplasts may be in their native state or dried by methods well known in the art, as long as it has integral membranes in order to protect from degradation the ATP produced in the presence of light. To avoid degradation and to be able to keep the liquid at room temperature, water (electron donor to initiate photosynthesis) and light must be restricted. Hence, the composition is preferably dried or dehydrated. If light is restricted, the composition may then be in an aqueous medium.

It will be understood by the skilled person that the carrier material may consist of a liquid or a solid carrier material. For example, the carrier material used to dissolve, suspend or mix the chloroplasts for ingestion can be a liquid, a powder, a gel, a cream etc. Particularly, the carrier material is safe for consumption and non-toxic upon ingestion by mammals. More particularly, the liquid is water. The composition, the carrier or the liquid may comprise a food coloring agent and/or a flavoring agent.

The amount of chloroplasts or portions thereof present in the composition may vary depending on the energy requirement of the subject. For example, the amount of chloroplasts may be measured by way of the ATP required after exposure to light. Alternatively, the amount of chloroplasts required may be evaluated on the basis of total chlorophylls present in the extract.

The concentration of chloroplasts present in solution can be expressed into equivalent total chlorophylls concentration. The total chlorophylls concentration can be from 0.01 ng/ml to 10 mg/ml, particularly, from 0.01 mg/ml to 1 mg/ml, still particularly from 0.025 to 0.5 mg/ml of solution.

Another aspect provides a method for the synthesis of fresh ATP to provide energy supplementation on demand. Particularly, the invention provides a method for the synthesis of ATP prior to ingestion/consumption by a subject for providing a source of energy. Amongst other applications, the energy supplementation method can also be useful in cell culture or bacterial culture.

In another aspect, there is provided the use of the composition as defined herein for the manufacture of an energy drink.

Another aspect of the invention provides the use of a plant extract or plant fraction as a source of ATP for the manufacture of an energy drink.

In a further aspect, there is also provided an energy drink comprising the composition as defined herein. Such energy drink may comprises a food coloring agent and/or a flavoring agent. In such drink, the amount of chloroplasts present in solution is preferably evaluated on the basis of total chlorophylls. The total chlorophylls in the solution may range preferably from 0.01 ng/ml to 10 mg/ml. Further, such energy drink preferably has a pH of 4.0-9.0 and more preferable of 6.8-7.4.

The dry chloroplasts could be contain in a dispensing cap. This cap must not let in light; which keeps latency ATP production. The cap is fixed to a bottle containing water and other ingredients. The pH of the liquid must be between 4.0 and 9.0, and preferably between 6.8 and 7.4. A buffer may be necessary to maintained the pH; it could be already in the liquid or in the preparation of dry chloroplasts.

The viscosity of the liquid or of the composition should preferably be maintain between 2 and 10 centipoise (cP); corresponding to a solution of 0.3 M sucrose (blood at 37° C. is 3-4 cP).

Another aspect of the invention provides an energy drink comprising the composition as described herein. Particularly, the energy drink is consisting of a liquid carried in a container that is protected from light and is suitable to be uncovered and then exposed to light immediately prior to ingestion.

Particularly, the container is translucent or transparent in order to let the light through. Particularly, the container is a bottle, more particularly a bottle with light resistant package suitable to be unpackaged such that the content of the bottle can be exposed to light prior to ingestion/consumption.

Alternatively, the quality of light to which the composition is exposed may affect the quantity of ATP produced by chloroplast. Hence, the container may be of different colors adapted to filter out certain colors to enhance the production of ATP. Particularly, the container is colorless. More particularly, the container is blue or red to filter out blue or red light.

More particularly, the container has the capacity to filter out light of the blue spectrum such as, for example, a filter that would block wavelengths below 400 nm and between 520 to 760 nm. Still more particularly, the container has the capacity to filter out light of the red spectrum such as, for example, a filter that would block wavelengths below 680 nm. Most particularly, the container is red.

In another aspect, there is provided with a kit comprising a container containing an aqueous carrier liquid and a pouch containing the composition as defined herein, in the form of a powder, wherein the powder is to be dissolved in the carrier liquid and the liquid is then exposed to light prior to ingestion/consumption.

BRIEF DESCRIPTION OF THE DRAWINGS

Having thus generally described the nature of the invention, reference will now be made to the accompanying drawings, showing by way of illustration, preferred embodiments thereof, and in which.

DETAILED DESCRIPTION OF THE INVENTION

Definitions

Figure 1:
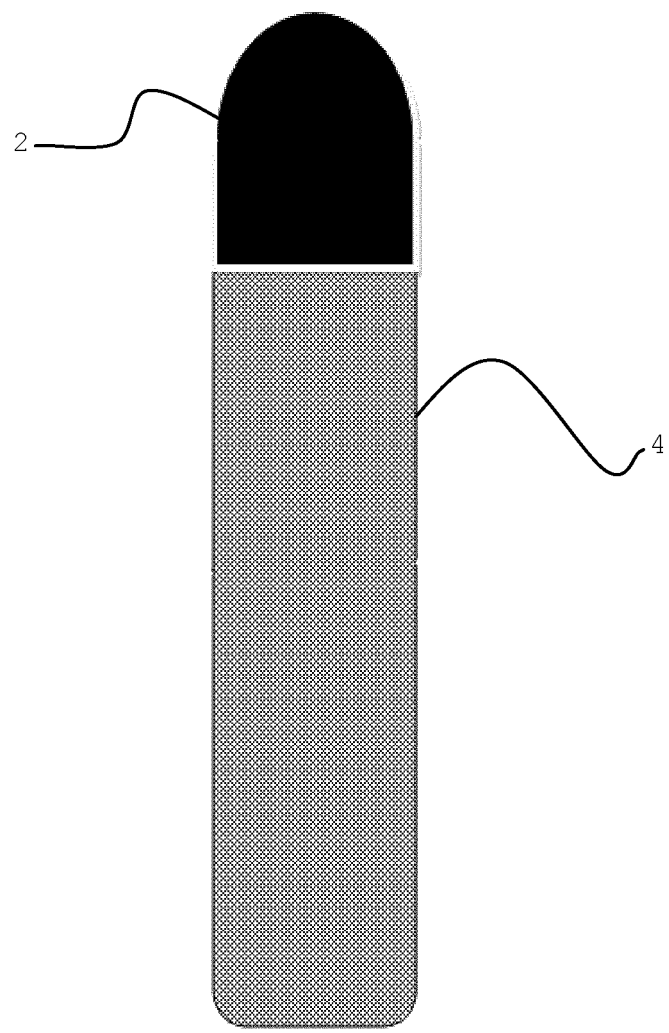
FIG. 1. Schematization of the container.

For the purpose of the present invention the following terms are defined below.

The expression "equivalent chlorophyll concentration" as used herein is the measurement unit representing the quantity of chloroplast, means the unit of chlorophyll-a plus chlorophyll-b, calculated according to the formula:

$$\text{Total chlorophylls} = \frac{[(7.15 \times \text{Absorbance at 663.2 nm}) + (18.71 \times \text{Absorbance at 646.8 nm})]}{1000};$$

This formula expresses total chlorophylls in mg/ml.

The expression "plant extract" as used herein is intended to mean any crude, processed or refined plant extract, including plant cell plastid. This can also mean any plant portion or derivative which can be used to obtain a plant extract, chloroplast (inner and outer membranes) or a mixture or a portion thereof.

The expression "Native ATP and native molecules" as used herein is intended to mean any molecule freshly synthesize in natural environment.

The expression "dehydrated" when made in reference to the composition is intended to mean that any aqueous medium in the composition has been remove by evaporation, freeze-drying, spray-drying or any other means available that would not substantially heat the composition so as to denature the chloroplasts or to destroy the photosynthesis activity of the composition.

The expression "aqueous medium" is used herein to refer to any water-containing solution or water-containing drink that would allow for the exchange of protons with water made during the photosynthetic process.

DETAILED DESCRIPTION OF PARTICULAR EMBODIMENTS

The present invention will now be described more fully hereinafter with reference to the accompanying drawings, in which preferred embodiments of the invention are shown. This invention, may, however, be embodied in many different forms and should not be construed as limited to the embodiments set forth herein; rather, these embodiments are provided so that this disclosure will be thorough and complete, and will fully convey the scope of the invention to those skilled in the art.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art.

The problem to which the present invention provides a solution, is to generate, in a liquid, a production of fresh (native) ATP and other molecules directly related by illumination by introducing a plant extract.

According to one embodiment of the present invention, there is provided a plant extract comprising chloroplasts, capable of synthesis ATP in function of illumination.

In one embodiment, the solution of the invention is generally composed of chloroplasts. The plant extract may also comprise a thylakoid system or extract.

Chloroplasts are membranous organelles that serve as the site of photosynthesis, and they have a major structural and functional importance for the present invention. Typically, chloroplasts comprise three types of membranes, which are: (i) a smooth outer membrane, which is freely permeable to molecules; (ii) a smooth inner membrane, which contains many transport proteins such as integral membrane proteins regulating the exchange of small molecules like sugars and proteins between the cytoplasm and the chloroplast; and (iii) a system of thylakoid membranes which contains the chlorophyll.

Chloroplasts extract can be obtained and characterized as taught in Hardt, H. and Kok, B. ((1978). Comparison of photosynthetic activities of spinach chloroplasts with those of corn mesophyll and corn bundle sheath tissue. Plant Physiol. 62, 59-63), incorporated herein by reference. Also, several different processes are known in the art for the preparation of chloroplasts.

It can be noted that plant fractions can be extracted from all plant species, including cyanobacteria, algae, bryophyta, and vascular plants. Every membrane fractions share the characteristic of having a double lipid layer linked to macromolecules such as structural or functional proteins. For photosynthetic materials, the chloroplast is commonly encountered in those organisms and thus represents a good choice, especially since pigments such as chlorophylls and carotenoids have the ability to bind to the photosynthetic membranes.

Chloroplasts are double membraned ATP-producing organelles found only in plants. Inside their outer membrane is a set of thin membranes organized into flattened sacs stacked up like coins called thylakoids. The disks contain chlorophyll pigments that absorb solar energy which is the ultimate source of energy for all the plant's needs including manufacturing carbohydrates from carbon dioxide and water (Mader, 1996, p. 75). The chloroplasts first convert the solar energy into ATP stored energy, which is then used to manufacture storage carbohydrates which can be converted back into ATP when energy is needed.

In one embodiment of the invention, the chloroplasts present in solution produce ATP, after illumination, are used as a component in an energy drink.

Chloroplasts could also be used as a source of instant energy in food, gels, cream and in different formulation.

Alternatively, another aspect of the invention provides a kit comprising a container containing a carrier liquid and a pouch containing the composition of the invention in the form of a powder, wherein the powder is to be dissolved in the carrier liquid and the liquid is then exposed to light prior to ingestion/consumption. As illustrated in FIG. 1, the composition of the invention could be confined in a dark cap 2 adapted to preserve the composition from light. There are powder-dispensing caps that exist in the art, that would be adapted for this use. The user, just before drinking the energy drink would simply release from the cap 2 the composition into the aqueous medium in the bottle 4 and expose it to light to initiate the photosynthesis process. The bottle should allow for light to pass through, such as a red or blue bottle.

In every cases chloroplasts, or mixture or part thereof, can be applied in a liquid through different methods. For example, but not limited to, the extracts of the present invention can be applied under form of an homogenate, a filtrate, a retentate, and can also be diluted or dried, at different concentrations of humidity, before application or use.

All patents, patent applications, articles and publications mentioned herein, both supra and infra, are hereby incorporated herein by reference. The present invention will be more readily understood by referring to the following examples, which are given to illustrate the invention rather than to limit its scope.

Example I

Purification of Plant Cell Plastid as an Active Ingredient in Energy Drink

Extract Preparation
Chloroplast Extract Preparation

The preparation of chloroplasts is a modified method from Hardt et al. (Hardt, 1978). The first step of the process involved the homogenization by mechanical grinding. The mesophylium tissues (leaves or needles) and stems were cut into small pieces with a rotative knife. The homogenization was performed between 0° C. and 40° C., but preferably under 4° C. to avoid any degradation of the tissue during the procedures. The tissue was homogenized in a homogenization buffer composed of 0.3 M sucrose, 50 mM Tris buffer (pH 7.4) and 10 mM sodium chloride. Taking spinach as a reference plant, the wet weight ratio of plant leaf tissues (g)/volume of buffer (ml) is of about ½ to ⅓. The plant is mixed with the buffer and homogenized for example, in a commercial blender for about 1 minute. When the plant source varies, the medium volume varies accordingly.

A separation step followed the homogenization step. Homogenates were separated from cell debris and soluble components by continuous centrifugation, at about 2000×g for 5 minutes or by applying the equivalent mechanical pressure. The centrifugation system allowed for the isolation of the homogenates based on their size, as the centrifugation means was provided with a 70 µm filter or its equivalent through which the homogenates was passed, but on which cell debris were retained. The pellet (chloroplasts) was suspended in homogenization buffer.

Example II

ATP Production by Chloroplasts Extract

Quantitative Bioluminescence Determination of ATP Produced by Chloroplasts

ATP produced by chloroplasts was consumed and light was emitted when firefly luciferase catalyzed the oxidation of D-luciferin:

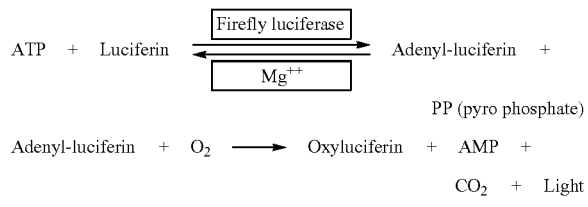

Light emission, directly proportional to ATP production, was detected by a luminometer.

The goal was to evaluate the relative ATP production in function to the residual ATP molecule already from chloroplasts. Upon illumination, chloroplasts continuously synthesized ATP molecules, so the quantity was presented on relative units because this was not a cumulative amount, but an ATP quantity after an illumination acquisition time. The quantity and quality of luciferin/luciferase was also important with respect to light emission. The acquisition time was fixed to 13 seconds.

Comparison of Different Source of Light (Natural and Artificial), Reading in Lux

| Clear night, full moon | — | 0.3 lux |
|---|---|---|
| — | Living rooms, offices | Approx. 250 lux |
| — | Classrooms, shops workshops | Approx. 500 lux |
| — | Drawing offices, precision workshops | Approx. 1000 lux |
| Winter's day, overcast sky | — | 900-2,000 lux |
| Winter's day, clear sky | — | up to 9,000 lux |
| Summer's day, overcast sky | — | 4,000-20,000 lux |
| Summer's day, clear sky | — | up to 100,000 lux |

Results of ATP Production after Illumination

Figure 2A:
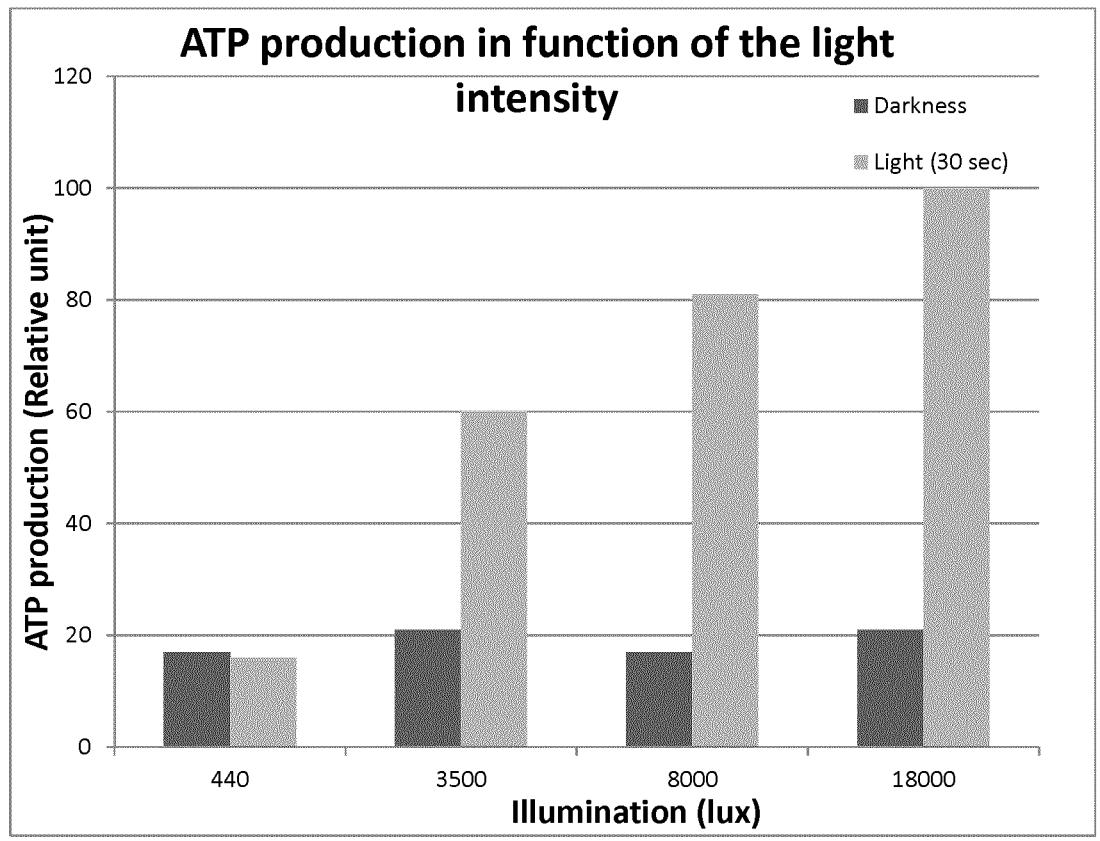
FIG. 2. a— illustrates the ATP production by chloroplast at 0.1 mg of total chlorophylls per ml of reactive media in function of the illumination intensity. b—illustrates the optimization of ATP production by light; ratio of the ATP production during illumination on darkness. Illumination time is 30 seconds.
Figure 2B:
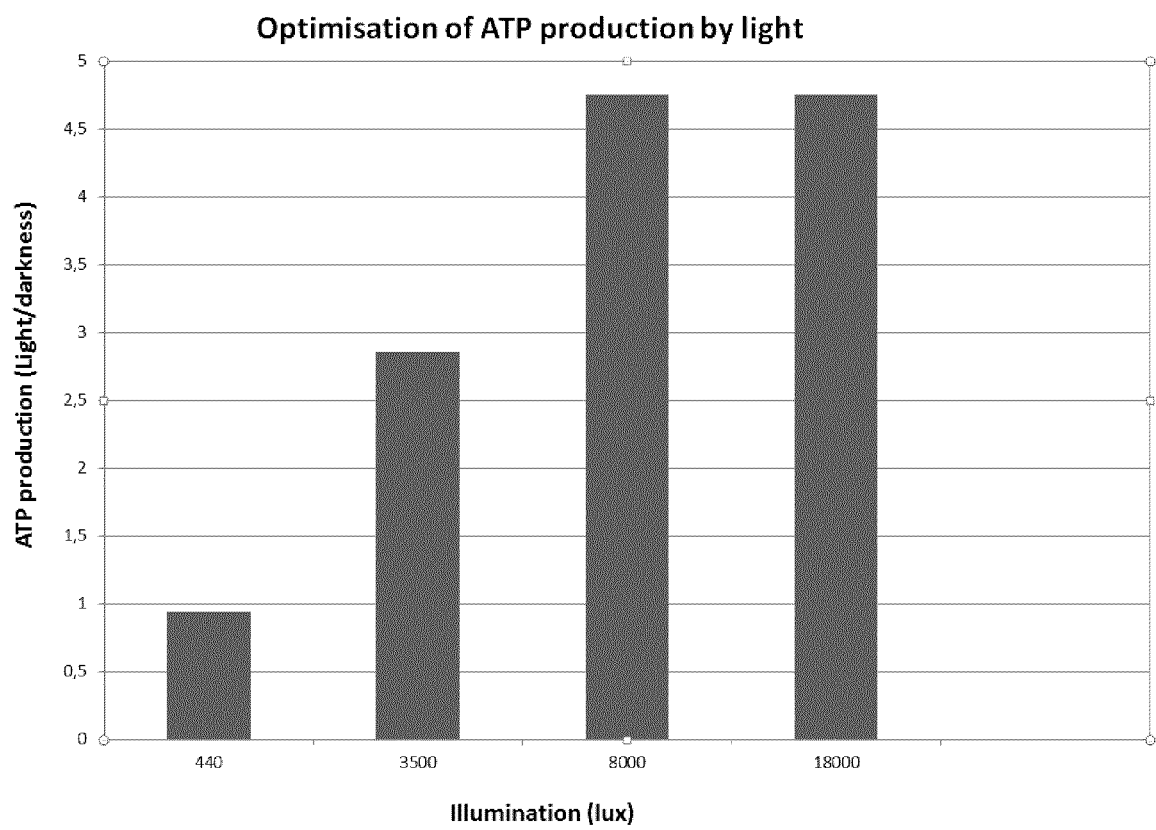

The chloroplasts (0.01 mg Chl/ml of phosphorus-containing solution) were illuminated 30 seconds prior to the acquisition data (13 seconds). At low irradiance (440 lux), there was no increase in ATP production in comparison to base ATP content. The ATP production increased 3, 4 and 5 times at 3500 lux, 8000 lux and 18000 lux, respectively (FIG. 2a). If we evaluate the optimization of ATP production by light by the ratio of the production after illumination and in darkness, we come to the conclusion that the optimum illumination is 8000 lux (FIG. 2a). With this concentration of chloroplast (0.01 mg Chl/ml of solution, there is no need to increase the intensity of light.

Figure 3:
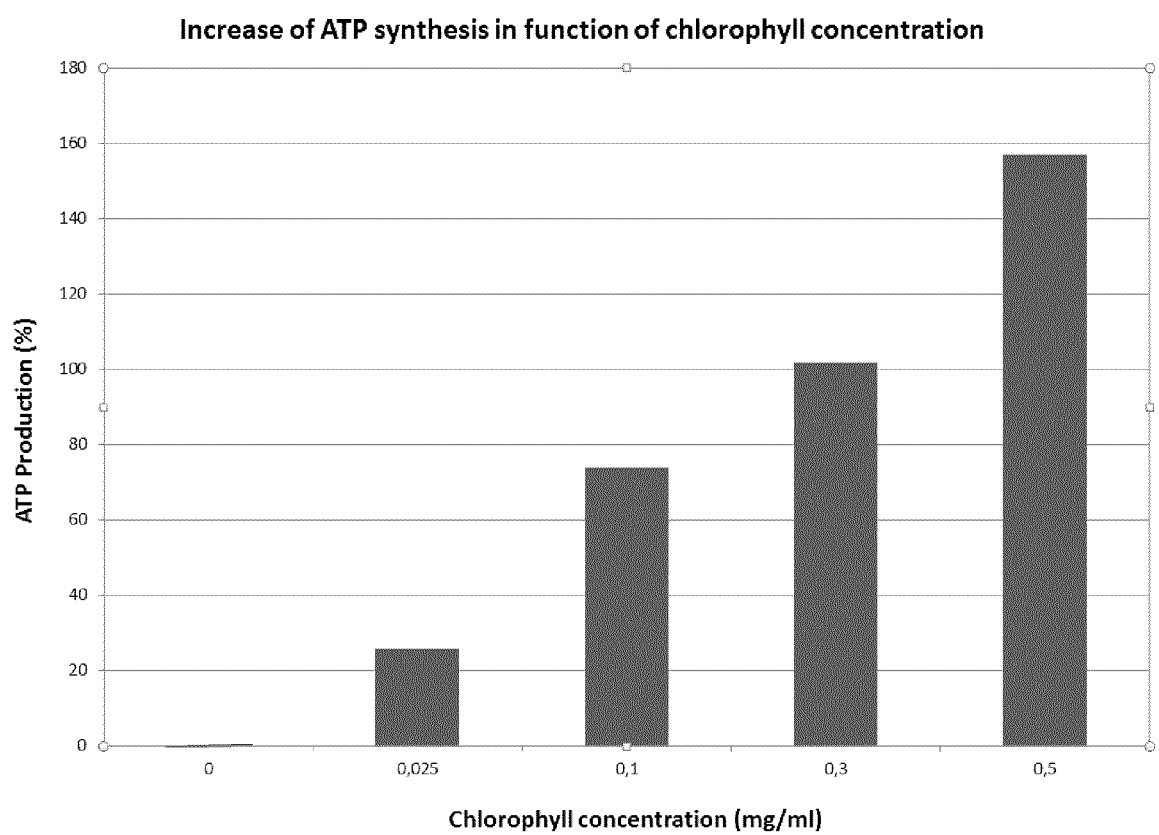
FIG. 3. illustrates the ATP increase by chloroplast in function of the concentration of chlorophylls in the media. Light intensity is 8000 lux. Illumination time is 30 seconds.

The ATP production increased in a dose-dependent manner. The concentration of chloroplasts was evaluated by the total chlorophylls (a and b) in solution. The percentage of ATP increase dramatically in comparison to the control in darkness (FIG. 3).

Figure 4:
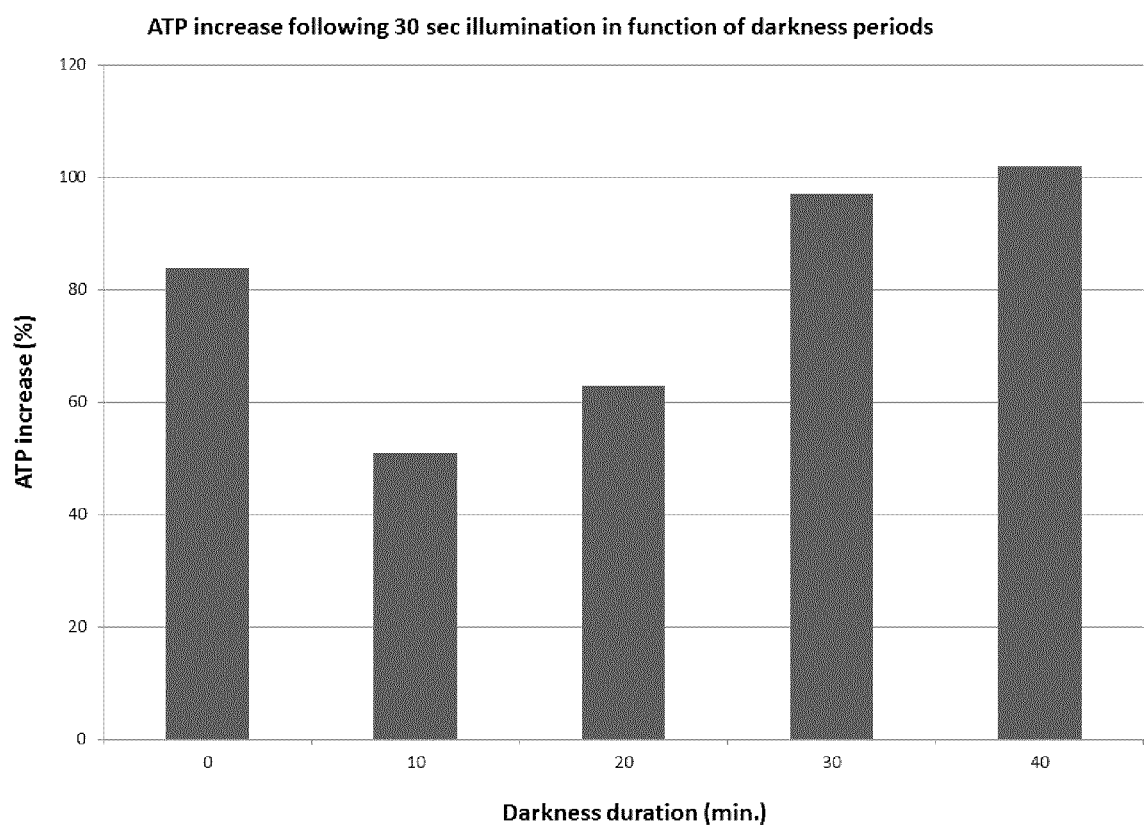
FIG. 4. illustrates the ATP increase by chloroplast in function of darkness periods. Illumination time is 30 seconds; Light intensity is 8000 lux; concentration of total chlorophylls is 0.1 mg/ml.
Figure 5:
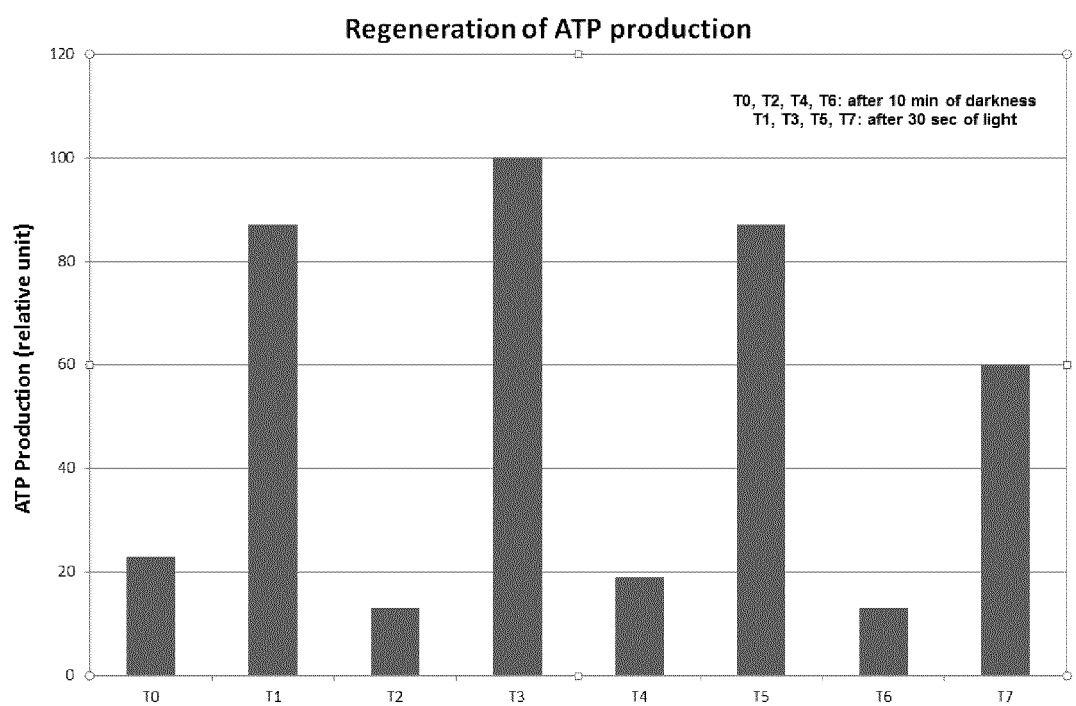
FIG. 5. illustrates the potential of the regeneration of the production of ATP by chloroplast in function of a darkness period (10 minutes). Illumination time is 30 seconds; Light intensity is 8000 lux; concentration of total chlorophylls is 0.1 mg/ml.

To investigate the capacity of chloroplasts to increase the ATP level after a long darkness period, we performed a test with successive illumination periods of 30 seconds followed by different periods of darkness (0 to 40 minutes). The ATP increased more, in function of a non-illuminated sample, with a longer darkness period, to a maximum of 40 minutes (FIG. 4). The chloroplasts had also the capacity to regenerate the production of ATP after successive periods of illumination. FIG. 5 illustrate the regeneration capability, in function of the control (T0), after 30 seconds of 8000 lux illumination and successive 10-minutes darkness periods. After 2 cycles (T1 and T3), the ATP production reached the maximum ATP production; the following cycles demonstrating large production of ATP but decrease in function of additional cycle.

Figure 6:
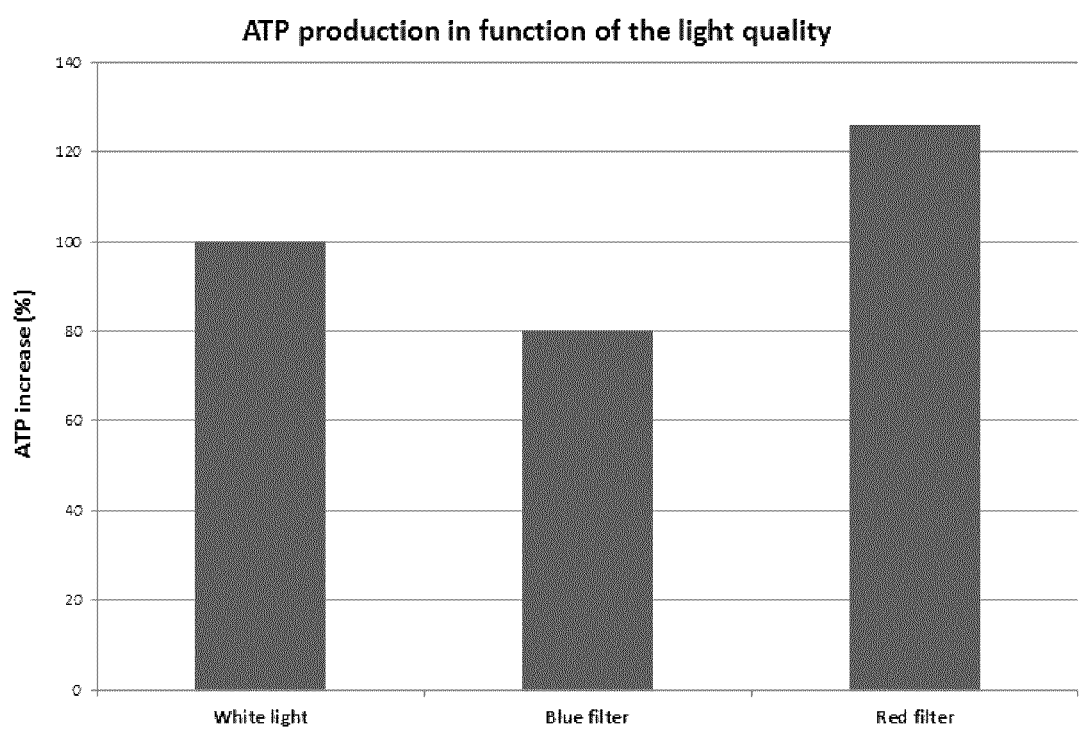
FIG. 6. illustrates the ATP increase by chloroplast in function of light quality (filter). Illumination time is 30 seconds; Light intensity is 3500 lux; concentration of total chlorophylls is 0.1 mg/ml.

The quality of light (blue and red filter in comparison of white light) could activate the phytochrome complex and initiate different inactivation/activation reactions. FIG. 6 illustrates that the ATP production after an illumination of 3500 lux during 30 seconds differs considerably between blue and red filter. In comparison to white light, red filter illumination, in these conditions, increased the ATP production by 25%.

Figure 7:
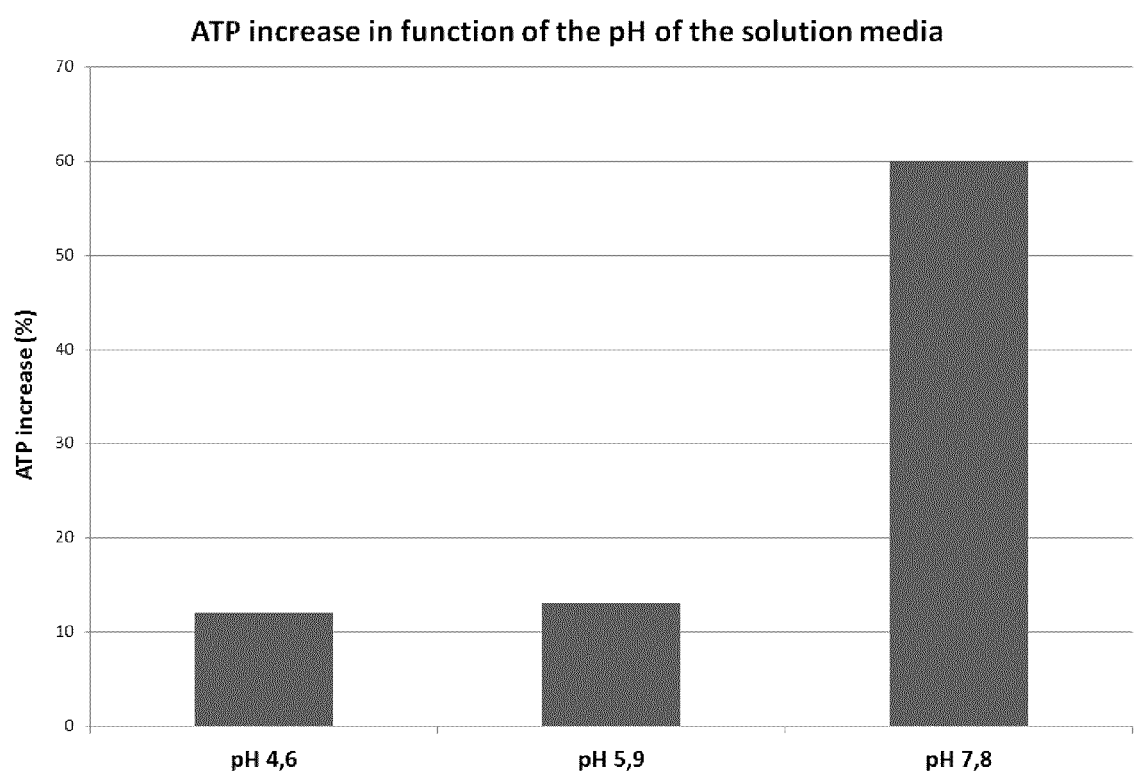
FIG. 7. illustrates the ATP increase by chloroplast in function of the pH of the solution media. Illumination time is 30 seconds; Light intensity is 3500 lux; concentration of total chlorophylls is 0.1 mg/ml.

At acid to lightly basic pH solutions (4.6 to 7.8), there was increased ATP production after a 30 seconds illumination at 3500 lux. In these conditions, a pH near the neutrality confers the best ATP production increase (FIG. 7).

To our knowledge, this is the first study demonstrating native ATP production, in natural condition (light, chlorophyll concentration . . . ), by the presence of a chloroplast extract in solution.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCE

Agteresch H. J., Dagnelie, P. C., Gaast, A. V. D., Stijnen, T. and Wilson J. H. P. (2000) Randomized clinical trial of adenosine 5'-triphosphate in patients with advanced non-small-cell lung cancer. J. Nat. Cancer Institute, 92: 321-328.

Allen J (2002). Photosynthesis of ATP-electrons, proton pumps, rotors, and poise. Cell 110 (3): 273-276.

Campbell, Neil A.; Brad Williamson; Robin J. Heyden (2006). Biologiy: Exploring Life. Boston, Mass.: Pearson Prentice Hall.

Dahout-Gonzalez C, Nury H, Trézéguet V, Lauquin G, Pebay-Peyroula E and Brandolin G (2006). Molecular, functional, and pathological aspects of the mitochondrial ADP/ATP carrier. Physiology (Bethesda) 21: 242-249.

Gajewski E, Steckler D, Goldberg R (1986). Thermodynamics of the hydrolysis of adenosine 5'-triphosphate to adenosine 5'-diphosphate. J Biol Chem 261 (27), 12733-12737.

Hardt H. and Kok B. (1978) Comparison of photosynthetic activities of spinach chloroplasts with those of corn mesophyll and corn bundle sheath tissue. Plant Phyiol. 62, 59-63.

Jäger, R., Michael D Roberts, Ryan P Lowery, Jordan M Joy, Clayton L Cruthirds, Christopher M Lockwood, John A Rathmacher, Martin Purpura and Jacob M Wilson. (2014). Oral adenosine-5'-triphosphate (ATP) administration increases blood flow following exercise in animals and humans. Journal of the International Society of Sports Nutrition, 11, 28.

Joyce C M and Steitz T A (1995). Polymerase structures and function: variations on a theme? J. Bacteriol. 177 (22): 6321-6329.

Mader, 1996, p. 75

Sprague R. S. et al., (1998) Deformation induced ATP release from red blood cells requires CFTR activity, Am. J. Physiol., 275, H1726-1732.

Sprague R. S. et al., (2001) Impaired release of ATP from red blood cells of human with primary pulmonary hypertension. Exp. Biol. Med., 226(5): 434-439.

Wilson, J M, Jordan M Joy, Ryan P Lowery, Michael D Roberts, Christopher M Lockwood, Anssi H Manninen, John C Fuller Jr., Eduardo 0 De Souza, Shawn M Baier, Stephanie M C Wilson and John A Rathmache (2013) Effects of oral adenosine-5'-triphosphate supplementation on athletic performance, skeletal muscle hypertrophy and recovery in resistance-trained men. Nutrition & Metabolism. 10, 57.

What is claimed is:

1. A dehydrated composition for energy supplementation in the form of ATP, the composition comprising isolated dehydrated chloroplasts and phosphorus, wherein the isolated dehydrated chloroplasts comprise functional thylakoid and chloroplastic membranes able to produce ATP in the presence of light.

2. The dehydrated composition of claim 1, wherein the dehydrated composition upon rehydration produces ATP upon exposure to light.

3. The dehydrated composition of claim 1, further comprising a carrier material.

4. The dehydrated composition of claim 1, further comprising a food coloring agent and/or a flavoring agent.

5. The dehydrated composition of claim 3, wherein the carrier material is a powder.

6. The dehydrated composition of claim 3, wherein the carrier material is a gel.

7. The dehydrated composition of claim 3, wherein the carrier material is a topical cream.

* * * * *